(12) United States Patent
Chalmers et al.

(10) Patent No.: US 7,095,511 B2
(45) Date of Patent: Aug. 22, 2006

(54) METHOD AND APPARATUS FOR HIGH-SPEED THICKNESS MAPPING OF PATTERNED THIN FILMS

(75) Inventors: Scott A. Chalmers, La Jolla, CA (US); Randall S. Geels, San Diego, CA (US)

(73) Assignee: Filmetrics, Inc., San Diego, CA (US)

( * ) Notice: Subject to any disclaimer, the term of this patent is extended or adjusted under 35 U.S.C. 154(b) by 0 days.

(21) Appl. No.: 09/899,383

(22) Filed: Jul. 3, 2001

(65) Prior Publication Data

US 2002/0030826 A1    Mar. 14, 2002

Related U.S. Application Data

(63) Continuation-in-part of application No. 09/611,219, filed on Jul. 6, 2000, now abandoned.

(51) Int. Cl.
*G01B 11/28* (2006.01)
(52) U.S. Cl. ...................................... 356/630
(58) Field of Classification Search ........ 356/630–632, 356/364–369; 427/8, 10, 248.1; 118/719, 118/724, 725
See application file for complete search history.

(56) References Cited

U.S. PATENT DOCUMENTS

| | | | | |
|---|---|---|---|---|
| 4,555,767 A | | 11/1985 | Case et al. ................ | 364/563 |
| 5,042,949 A | * | 8/1991 | Greenberg et al. .......... | 356/451 |
| 5,291,269 A | * | 3/1994 | Ledger ....................... | 356/504 |
| 5,436,725 A | * | 7/1995 | Ledger ....................... | 356/504 |
| 5,609,511 A | * | 3/1997 | Moriyama et al. ............ | 451/5 |
| 5,686,993 A | * | 11/1997 | Kokubo et al. ............. | 356/630 |
| 5,747,813 A | | 5/1998 | Norton et al. ............... | 250/372 |
| 5,856,871 A | * | 1/1999 | Cabib et al. ................ | 356/503 |
| 6,162,010 A | * | 12/2000 | Ishizawa et al. ............ | 414/805 |

FOREIGN PATENT DOCUMENTS

| | | |
|---|---|---|
| EP | 0 644 399 A2 | 3/1995 |
| EP | 0 652 415 A1 | 5/1995 |
| EP | 0 663 265 A1 | 7/1995 |
| JP | 411220004 A * | 8/1999 |

OTHER PUBLICATIONS

Jones, G.R. et al., *Chromatic Interferometry for an Intelligent Plasma Processing System*, Measurement Science & Technology, vol. 5, No. 6, Jun. 1994, pp. 639-647, XP 000456344; Bristol, GB.

(Continued)

*Primary Examiner*—Hoa Q. Pham
(74) *Attorney, Agent, or Firm*—Courtney Staniford & Gregory LLP

(57) ABSTRACT

A system is described that permits high-speed, high-resolution mapping of thicknesses (or other properties) of layers on patterned semiconductor wafers. The system comprises one or more spectrometers that each simultaneously image a plurality of spatial locations. In one example, the spectrometer comprises a two-dimensional CCD imager with one axis of the imager measuring spectral data and the other axis measuring spatial data. Spectral reflectance or transmission of the patterned wafer under test is obtained by passing the wafer under (or over) the imaging spectrometer(s) and taking sequential reflectance or transmission images for successive pluralities of spatial locations. The resulting spectral reflectance or transmission map can then be analyzed at discrete locations to determine the thicknesses or other properties of the layers at those locations.

17 Claims, 13 Drawing Sheets

OTHER PUBLICATIONS

Lange, V. et al., *Reflexionsinterferometrie zur Kontrolle dünner Silizium-Membranen, Technisches Messen*, vol. 61, No. 9, Sep., 1994, pp. 346-351, XP000465894, pp. 346-351, figures 1-4.

*ImSpector* Imaging Spectrograph brochure including specifications, Spectral Imaging Ltd., Oulu, Finland, (3 pages).

CCD Detectors, Optical Systems Division, retrieved on-line Jun. 21, 2000, (3 pages).

*Advanced Thin Film Measurements—About thin Film*, Filmetrics, retrieved on-line Jun. 21, 2000; pp. 1-6.

*Advanced Thin Film Measurements—Operation*, Filmetrics, retrieved on-line Jun. 21, 2000; pp. 1-2.

*Advanced Thin Film Measurements—PTFEON Data*, Filmetrics, retrieved on-line Jun. 21, 2000; (1 page).

*Advanced Thin Film Measurements—faq*, Filmetrics, retrieved on-line Jun. 21, 2000; (2 pages).

J.B. Wellman, Imaging Spectrometers for Terrestrial and Planetary Remote Sensing, SPIE Proceedings, vol.: 750, p. 140 (1987).

R. W. Basedow, "Hydice: Operational System Status," NASA, ISSSR-95 (1995).

* cited by examiner

METHOD AND APPARATUS FOR HIGH-SPEED THICKNESS MAPPING OF PATTERNED THIN FILMS

This application is a continuation-in-part of U.S. patent application Ser. No. 09/611,219, filed Jul. 6, 2000, now abandoned, which is hereby fully incorporated by reference herein as though set forth in full.

I. BACKGROUND OF THE INVENTION

This invention relates generally to the field of film thickness measurement, and more specifically, to the field of film measurement in an environment, such as semiconductor wafer fabrication and processing, in which the layer whose thickness is desired to be measured resides on a patterned sample.

Many industrial processes require precise control of film thickness. In semiconductor processing, for example, a semiconductor wafer is fabricated in which one or more layers of material from the group comprising metals, metal oxides, insulators, silicon dioxide ($SiO_2$), silicon nitride (SiN), polysilicon or the like, are stacked on top of one another over a substrate, made of a material such as silicon. Often, these layers are added through a process known as chemical vapor deposition (CVD), or removed by etching or removed by polishing through a process known as chemical mechanical polishing (CMP). The level of precision which is required can range from 0.0001 µm (less than an atom thick) to 0.1 µm (hundreds of atoms thick).

To determine the accuracy of these processes after they occur, or to determine the amount of material to be added or removed by each process, it is advantageous to measure the thickness of the layers that are on each product wafer (i.e., on each wafer produced that contains saleable product), which is generally patterned with features on the order of 0.1 µm to 10 µm wide. Because the areas covered by these features are generally unsuitable for measurement of film properties, specific measurement "pads" are provided at various locations on the wafer. To minimize the area on the wafer that is taken up by these measurement pads, they are made to be very small, usually about 100 µm by 100 µm square. This small pad size presents a challenge for the film measurement equipment, both in measurement spot size and in locating the measurement pads on the large patterned wafer.

To date, though its desirable effects on product yield and throughput are widely recognized, thickness measurements are only made after certain critical process steps, and then generally only on a small percentage of wafers. This is because current systems that measure thickness on patterned wafers are slow, complex, expensive, and require substantial space in the semiconductor fabrication cleanroom.

The most widely used technique for measuring thin-film thickness on both patterned and unpatterned semiconductor wafers is spectral reflectance. Conventional systems for measuring thickness on patterned wafers employ high-magnification microscope optics along with pattern recognition software and mechanical translation equipment to find and measure the spectral reflectance at predetermined measurement pad locations. Examples of this type of system are those manufactured by Nanometrics, Inc., and KLA-Tencor. Such systems are too slow to be used concurrently with semiconductor processing, so the rate of semiconductor processing must be slowed down to permit film monitoring. The result is a reduced throughput of semiconductor processing.

A newer method for measuring thickness of patterned films is described in U.S. Pat. No. 5,436,725. This method uses a CCD camera to image the spectral reflectance of a full patterned wafer by sequentially illuminating the wafer with different wavelengths of monochromatic light. Because the resolution and speed of available CCD imagers are limited, higher magnification sub-images of the wafer are required to resolve the measurement pads. These additional sub-images require more time to acquire and also require complex moving lens systems and mechanical translation equipment. The result is questionable advantage in speed and performance over traditional microscope/pattern recognition-based spectral reflectance systems.

Accordingly, it is an object of the present invention to provide a method and apparatus for achieving rapid measurement of film thickness and other properties on patterned wafers during, between, or after semiconductor processing steps.

An additional object is a method and apparatus for film measurement which is capable of providing an accurate measurement of film thickness and other properties of individual films in a multi-layered or patterned sample.

A further object is an optical method and apparatus for thin-film measurement which overcomes the disadvantages of the prior art.

Further objects of the subject invention include utilization or achievement of the foregoing objects, alone or in combination. Additional objects and advantages will be set forth in the description which follows, or will be apparent to those of ordinary skill in the art who practice the invention.

II. SUMMARY OF THE INVENTION

The invention provides a system for measuring one or more properties of a film. A light source is configured to direct light to the film. A one-dimensional imaging spectrometer is configured to receive light reflected from or transmitted through a one dimensional pattern of spatial locations on the film, and determine therefrom a reflectance or transmission spectrum for one or more of the spatial locations in the pattern. The spectrometer may be configured to provide resolution of 1 mm or better along both first and second spatial dimensions.

A translation mechanism is configured to relatively translate the film with respect to the spectrometer or the spectrometer and the light source. A processor is configured to (a) obtain from the spectrometer reflectance or transmission spectra for a plurality of one dimensional patterns of spatial locations along the film; (b) aggregate these reflectance or transmission spectra to obtain reflectance or transmission spectra for a two dimensional area on the film, the reflectance or transmission spectra for the two dimensional area having spatial resolution of 1 mm or better; and (c) determine therefrom one or more properties of the film.

The invention also provides a method for measuring one or more properties of a film. Light is directed to the film, whereupon it reflects from or is transmitted through a one dimensional pattern of spatial locations on the film. The reflected or transmitted light is received, and a reflectance or transmission spectrum determined therefrom for one or more of the one dimensional spatial locations in the pattern.

Reflectance or transmission spectra for additional one dimensional patterns of spatial locations on the film are also received. These reflectance or transmission spectra are aggregated to obtain reflectance or transmission spectra for a two dimensional area on the film, the reflectance or transmission spectra for the area having spatial resolution of 1 mm or better. One or more properties of the film may then be determined from the reflectance or transmission spectra for the two dimensional area.

In one embodiment, the spectrometer is configured to concurrently or simultaneously capture a reflectance or transmission spectrum for each of a plurality of spatial locations on the sample. The spectrometer includes a wavelength-dispersive element, such as a prism or diffraction grating, for receiving in parallel light reflected from or transmitted through the plurality of spatial locations, and concurrently or simultaneously separating the light for each such location into its constituent wavelength components. The spectrometer further includes an imager for receiving the constituent wavelength components for each of the locations, and determining therefrom the reflectance or transmission spectrum for each location.

In one implementation, the system is configured to measure at least one film on a sample from light reflected from or transmitted through the sample having a plurality of wavelength components, each having an intensity. A set of successive, spatially-contiguous, one-spatial-dimension spectral reflectance or transmission images may be obtained by scanning the wafer with a one-spatial-dimension spectroscopic imager. The resulting series of one-spatial-dimension spectral images may be arranged to form a two-spatial-dimension spectral image of the wafer. The spectral data at one or more of the desired measurement locations may then be analyzed to determine a parameter such as film thickness.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

III. BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

IV. DETAILED DESCRIPTION OF THE PREFERRED EMBODIMENTS

Figure 1:
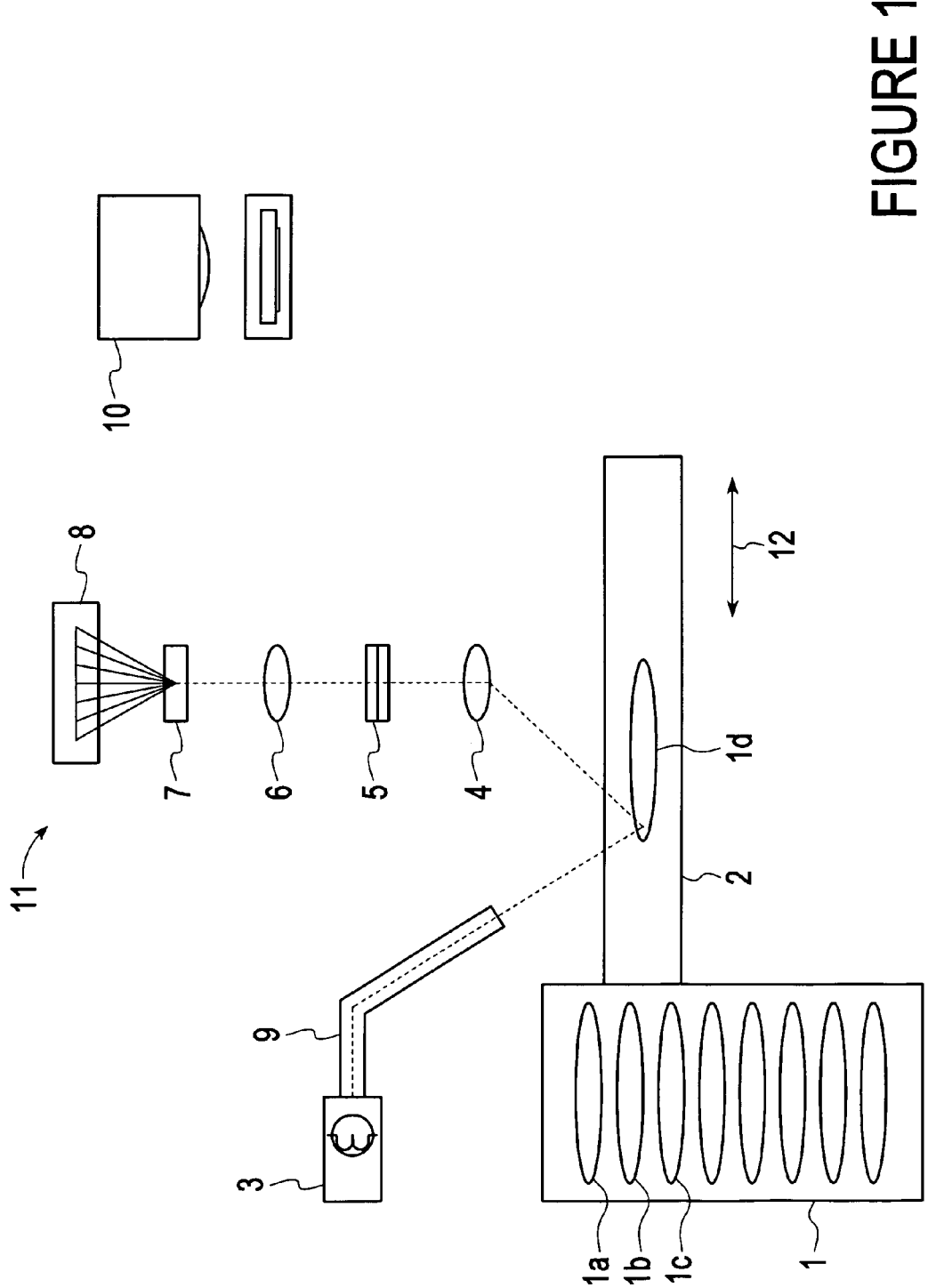
FIG. 1 illustrates a first embodiment of a system in accordance with the subject invention.

A first embodiment of an imaging system in accordance with the subject invention, suitable for use in applications such as measuring the thickness of transparent or semi-transparent films, is illustrated in FIG. 1. Advantageously, the film to be measured ranges in thickness from 0.001 µm to 50 µm, but it should be appreciated that this range is provided by way of example only, and not by way of limitation. This embodiment is advantageously configured for use with a wafer transfer station 1 to facilitate rapid measurement of a cassette of wafers. The station houses a plurality of individual wafers 1a, 1b, 1c, and is configured to place a selected one of these wafers, identified with numeral 1d in the figure, onto platform 2. This embodiment also comprises a light source 3 coupled to an optical fiber 9 or fiber bundle for delivering light from the light source 3 to the wafer 1d situated on platform 2. Preferably, the light source 3 is a white light source. Advantageously, the light source 3 is a tungsten-halogen lamp or the like in which the output is regulated so that it is substantially invariant over time. For purposes of illustration, this embodiment is shown being used to measure the thickness of film on wafer 1d, which together comprises a sample, but it should be appreciated that this embodiment can advantageously be employed to measure the thickness of individual films in samples comprising multi-layer stacks of films.

Also included is a line imaging spectrometer 11 comprising a lens assembly 4, slit 5, lens assembly 6, diffraction grating 7, and two-dimensional imager 8. The line imaging spectrometer operates as follows. Light from source 3 passes through fiber bundle 9, and impinges on a film contained on or in wafer 1d. The light reflects off the wafer and is received by lens assembly 4. Lens assembly 4 focuses the light on slit 5. Slit 5 receives the light and produces a line image of a corresponding line on the wafer 1d. The line image is arranged along a spatial dimension. The line image is received by second lens assembly 6 and passed through diffraction grating 7.

Diffraction grating 7 receives the line image and dissects each subportion thereof into its constituent wavelength components which are arranged along a spectral dimension. In one implementation, the spectral dimension is perpendicular to the spatial dimension. The result is a two-dimensional spectral line image which is captured by two-dimensional imager 8. In one implementation, the imager is a CCD, the spatial dimension is the horizontal dimension, and the spectral dimension is the vertical dimension. In this implementation, the spectral components at each horizontal CCD pixel location along the slit image is projected along the vertical dimension of the CCD array.

Figure 2:
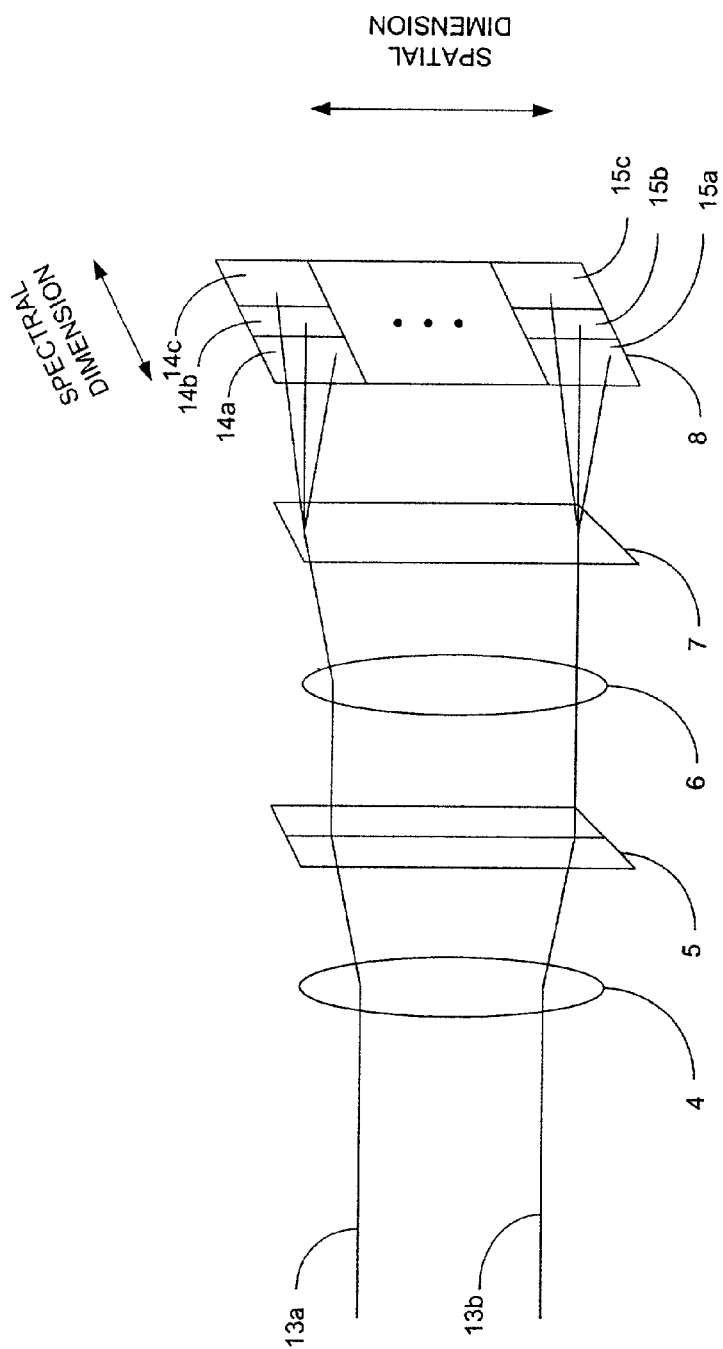
FIG. 2 illustrates in detail the optical subsystem of the FIG. 1 embodiment.

Additional detail regarding the spectrometer 11 is illustrated in FIG. 2 in which, compared to FIG. 1, like elements are referenced with like identifying numerals. As illustrated, reflected light (for purposes of illustration, two rays of reflected light, identified with numerals 13a and 13b are shown separately) from wafer 1d is received by lens assembly 4 and focused onto slit 5. Slit 5 forms a line image of the light in which the subportions of the line image are arranged along a spatial dimension. The line image is directed to lens assembly 6. Lens assembly 6 in turn directs the line image to diffraction grating 7. Diffraction grating 7 dissects each subportion of the line image into its constituent wavelength components. The wavelength components for a subportion of the line image are each arranged along a spectral dimension. The wavelength components for the subportions of the line image are individually captured by two-dimensional imager 8. Thus, the wavelength components for ray 13a are individually captured by pixels 14a, 14b, and 14c, respectively. Similarly, the wavelength components for ray 13b are individually captured by pixels 15a, 15b, and 15c, respectively.

With reference to FIG. 1, the light source 3 and the platform 2 are moveable relative to one another. In addition, the platform 2 and spectrometer 11 are moveable in relation to one another. In one implementation, the light source 3 and spectrometer 11 are stationary, and the platform is moveable in the X direction 12.

In operation, light from the fiber bundle 9 is reflected off of the wafer 1d on platform 2 on the wafer transfer station 1. The light is detected by the one-spatial-dimension imaging spectrometer 11, which in turn communicates the spectral and spatial information to the computer 10 over one or more signal lines or through a wireless interface. Spectral reflectance data is continually taken in this way while the wafer 1d is moved under the one-spatial-dimension imaging spectrometer by the platform 2. Once the entire wafer has been scanned in this manner, the computer 10 uses the successively obtained one-dimensional spatial data to generate a two-spatial-dimension image of the wafer. This two-dimensional map can be generated by assembling the measured signal intensity at a single wavelength at each location on the wafer into an image. This two-dimensional image can then be used to find pixels that correspond to specific locations on the wafer, and then the spectral reflectance data that is associated with these pixels can be analyzed using suitable techniques to arrive at an accurate estimate of the thickness of the film. Typically, film thickness is determined by matching the measured spectrum to a theoretically or experimentally determined set of spectra for layers of different thicknesses.

In the foregoing embodiment, although a CCD-based one-spatial-dimension imaging spectrometer is illustrated and described as the means for determining the intensity of the reflected light as a function of wavelength, it should be appreciated that other means are possible for performing this function, and other types of one-spatial-dimension imaging spectrometers are possible than the type illustrated in the figure.

Although the foregoing embodiment is described in the context of semiconductor wafers, and is illustrated in combination with a wafer transfer station for performing this function, it should be appreciated that it is possible to employ this embodiment in other contexts and in combination with other processing apparatus. Other possible applications include providing thin film scratch resistant and/or antireflective optical coatings to automotive plastics, eyeglass lenses, and the like plastics packaging applications, and applications involving providing proper polymide and resist thicknesses for flat panel display manufacturing. In fact, any application or industrial process in which film measurement is desired is possible for use with the subject embodiment.

Among the primary advantages of the foregoing embodiment is that it is particularly well-suited for real-time applications. The reason is that data collection steps employing time-consuming angular or mechanical sweeps of optical components as found in the prior art are eliminated. For example, in the subject embodiment, the one-spatial-dimension imaging spectrometer directly provides digitized values of intensity of the incoming light as a function of wavelength without requiring mechanical sweeping steps or the like. Also, digital CCD-based line-scan cameras are available with sufficient numbers of pixels so that resolution of measurement pads is practically possible. In addition, the number of analytical and pattern recognition steps performed by the computer are limited to only a very few. This is because an image of the entire wafer is made, which eliminates complicated pattern recognition routines that are needed when only small areas of the wafers are viewed at any one time, such as is the case with microscope-based instruments.

Figure 3:
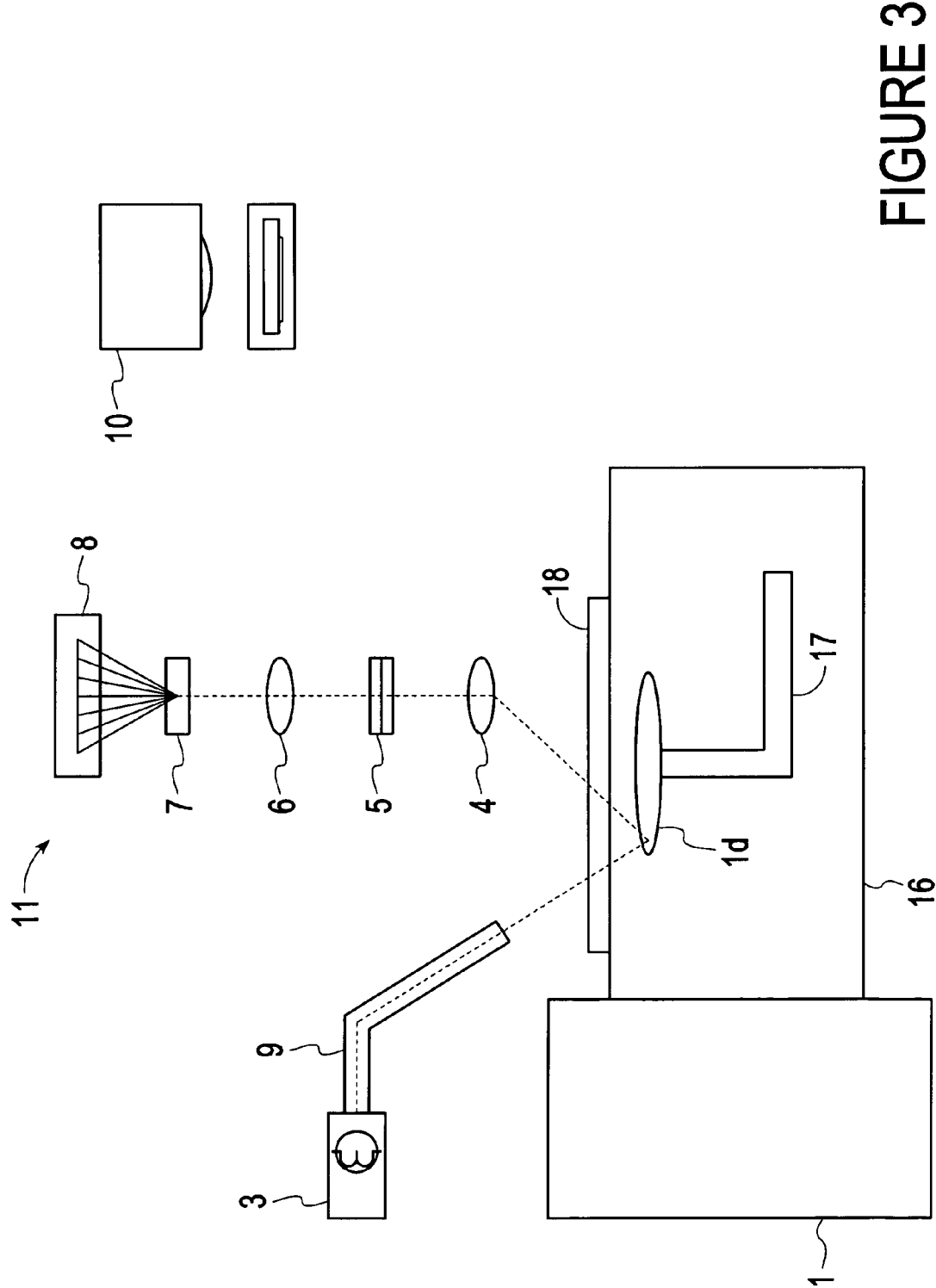
FIG. 3 illustrates a second embodiment of a system in accordance with the subject invention.

A second embodiment of the subject invention, suitable for measuring transparent or semi-transparent films, such as dielectrics deposited upon patterned semiconductor wafers, is illustrated in FIG. 3, in which, compared to FIGS. 1–2, like elements are referenced with like identifying numerals. This embodiment is similar to the previous embodiment, with the exception that the wafer id is in a vacuum process or transfer chamber 16, and the wafer motion required for scanning is provided by the transfer robotics 17 that are used to move the wafer inside the process chamber assembly. These transfer robotics allow the wafer 1d to move in the X direction relative to light source 3 and spectrometer 11. Visual access to the wafer 1d is provided by viewport 18. More specifically, light from light source 3 is directed to impinge upon wafer 1d via fiber bundle 9 through viewport 18. In addition, light reflected from wafer 1d is received by spectrometer 11 after passage through viewport 18. As transfer robotics 17 move the wafer 1d through the transfer station 16 as part of the CVD process, spectral measurements are successively taken from successive portions of wafer 1d and provided to processor 10. Processor 10 may successively perform calculations on the data as it is received or may do so after all or a substantial portion of the wafer 1d has been scanned. As with the previous embodiment, processor 10 may use this data to estimate film thickness.

In addition to the advantages listed for the first embodiment, this embodiment has the additional advantage of providing rapid in-line film thickness measurements taken during the normal transfer motion of the wafers between processes. This means that measurements can be made without slowing down the process and thus will not negatively impact throughput. Also, because the unit is compact and can be placed upon existing equipment, very little cleanroom space is required. Additionally, because there are no added moving parts, the system is very reliable. Moreover, because it sits entirely outside of the vacuum chamber, it introduces no particles or contamination to the fabrication process.

Although the foregoing embodiment is described in the context of CVD processing of semiconductor wafers, and is illustrated in combination with a CVD station for performing this function, it should be appreciated that it is possible to employ this embodiment in other contexts and in combination with other processing apparatus. In fact, any application or industrial process in which in-line film measurement is desired, i.e., film measurement during an ongoing industrial process, is possible for use with the subject embodiment.

Figure 4:
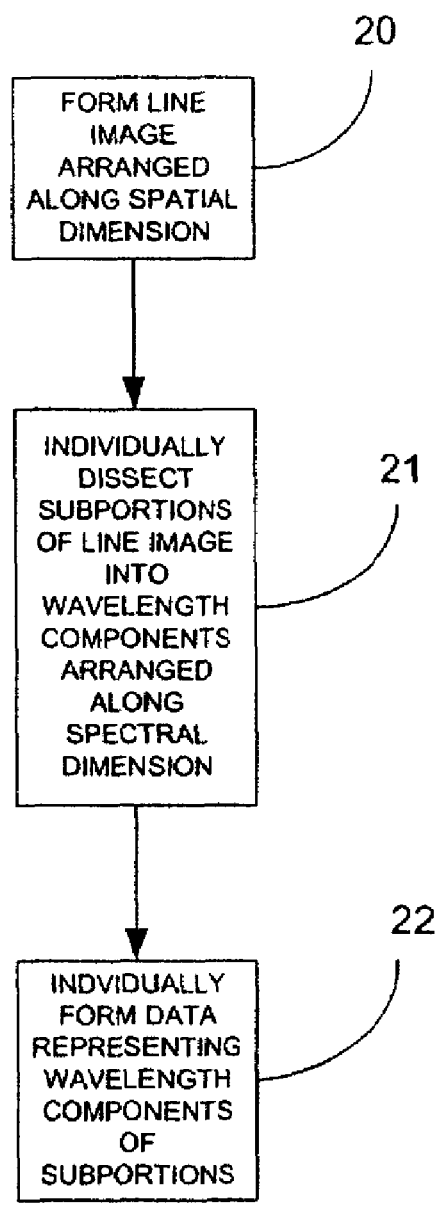
FIG. 4 illustrates an embodiment of a method in accordance with the subject invention.

An embodiment of a method in accordance with the invention is illustrated in FIG. 4. As illustrated, in step 20, a line image of a corresponding line of a film is formed. The line image has subportions arranged along a spatial dimension. Step 20 is followed by step 21, in which subportions of the line image are individually dissected to their relevant constituent wavelength components. The wavelength components for a subportion are arranged along a spectral dimension. Step 21 is followed by step 22, in which data representative of the wavelength components of the subportions is individually formed. The process may then be repeated for successive lines of the film until all or a selected portion of the film has been scanned. Throughout or at the conclusion of this process, estimates of film thickness or other film properties may be formed from the assembled data.

EXAMPLES

In an example embodiment of the subject invention, suitable for use in a CVD environment, the light source 3 is a tungsten/halogen regulated light source, manufactured by Stocker & Yale, Inc., Salem, N.H.

Fiber/fiber bundle 9 in this embodiment is a bundle configured into a line of fibers to provide uniform illumination along the measured surface. Such a fiber optic "line light" is manufactured by several companies, Stocker & Yale being a prime example.

This example is configured for use with CVD processing system Model P5000 manufactured by Applied Materials Inc., Santa Clara, Calif. An optically clear viewport 18 is provided in the standard P5000 configuration.

The line imaging spectrometer 11 in this example is manufactured by Filmetrics, Inc., San Diego, Calif., the assignee of the subject application. In this spectrometer, the imager 8 is a CCD imager incorporating a time delay and integration line scan camera manufactured by Dalsa Inc., Part No. CT-E4-2048 which has a CCD imager that has 2048 pixels in the system spatial direction, and 96 pixels in the system spectral direction. The transmission diffraction grating 7 is manufactured by Optometrics, Ayer, Mass., Part No. 34-1211. The lenses 4 and 6 are standard lenses designed for use with 35 mm-format cameras. The line scan camera is operated in area scan mode, with only the first 48 rows of pixels read out. This results in a data read rate greater than 700 frames per second. Forty-eight rows of spectral data are sufficient for measurement of thicknesses in the range required for CVD deposited layers.

It has been found that this example embodiment yields a thickness accuracy of +1 nm at a 1000 nm film thickness, at a rate of five seconds per wafer scan.

A commercial embodiment of a system according to the invention will now be described. The manufacturers of the components of this system are as identified in the previous exception, with the exception of the lens assembly used in the spectrometer. In lieu of standard lenses designed for use with 35 mm. cameras, high quality lenses and mirrors manufactured by Optics 1 in Thousand Oaks, Calif., are used. These lenses and mirrors are such that the modulation transfer function (MTF) for a plurality of alternating black and white line pair having a density of about 40 line pairs/mm. is greater than 70% over the entire wavelength range of interest.

This system is configured to measure the thicknesses of individual layers of a sample, e.g., patterned semiconductor wafer, at desired measurement locations. The coordinates of these desired measurement locations are provided to the system. Rather than rely on complicated and unreliable traditional pattern recognition techniques to find the exact measurement locations, the thickness of the wafer at each of these desired locations is determined by comparing the actual reflectance spectra for locations in a larger area containing the desired measurement location with a modeled reflectance spectra for the area assuming a particular layer thickness. If the comparison is within a desired tolerance, the assumed thickness is taken to be the actual thickness. If the comparison is not within the desired tolerance, the assumed thickness is varied, and the modeled reflectance spectra redetermined consistent with the newly assumed thickness. This process is continued until a comparison is performed which is within the desired tolerance. This process is repeated for a predetermined number, e.g. 5, of desired measurement locations on a layer of the wafer.

Figure 5A:
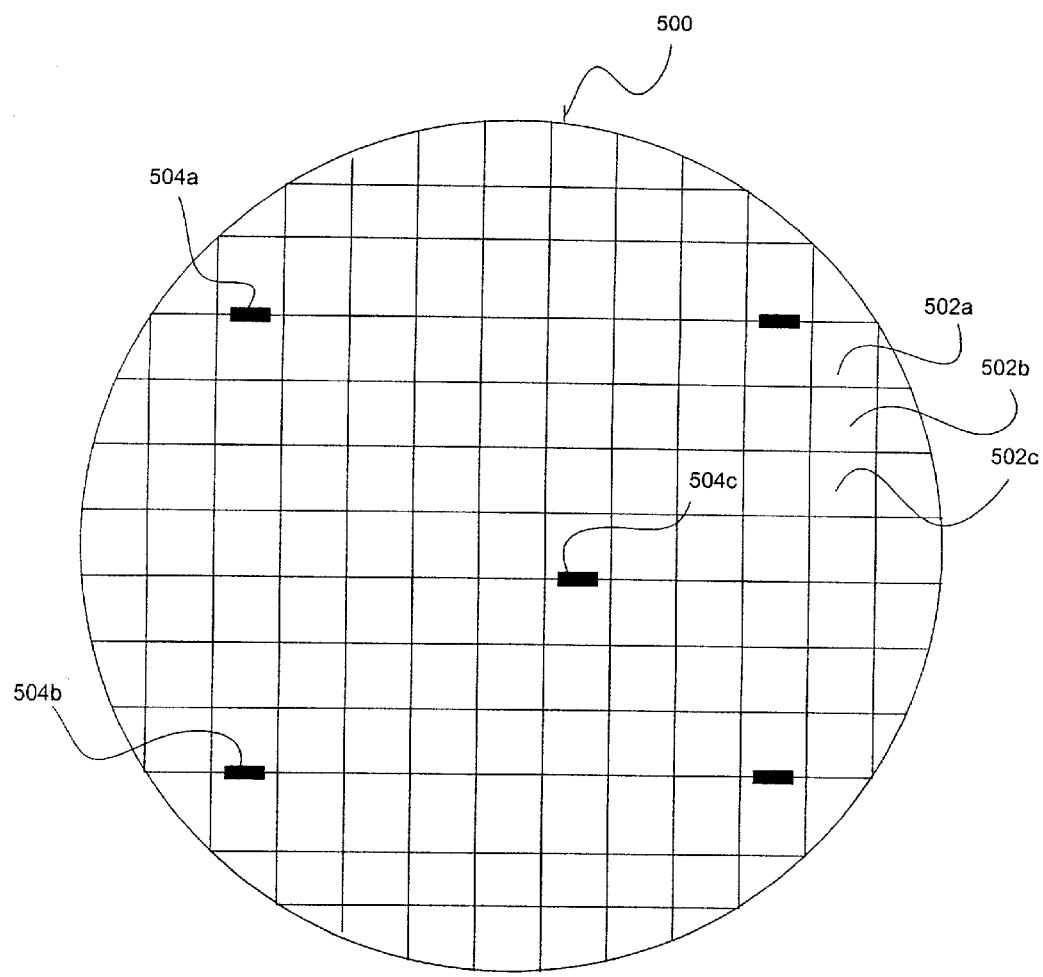
FIG. 5A is a top view of an example semiconductor wafer showing desired measurement locations.
Figure 5B:
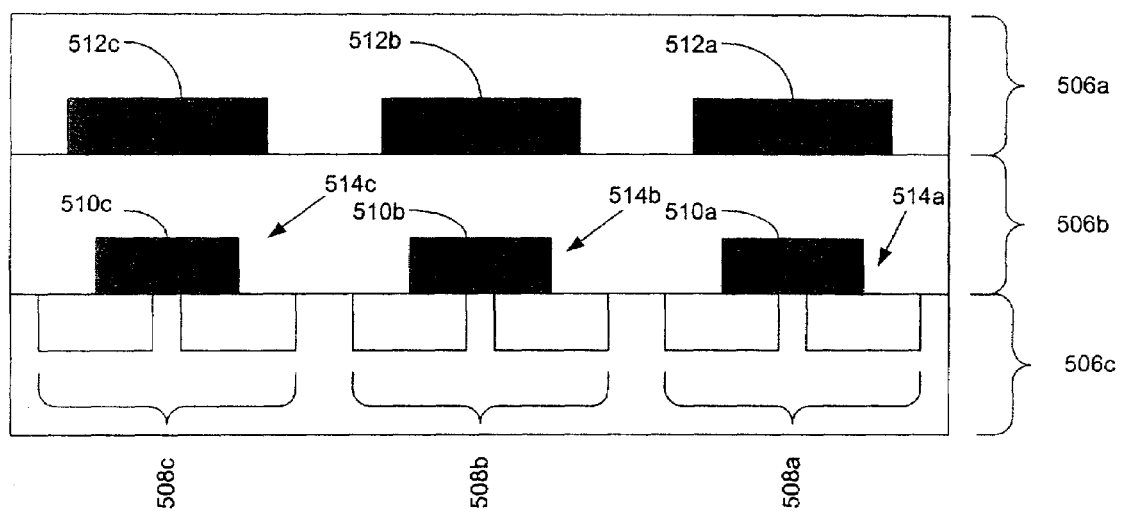
FIG. 5B is a side view of an example semiconductor wafer showing stacked layers each configured with one or more precise features.

The situation can be further explained with reference to FIGS. 5A and 5B, which illustrate different views of an example 500 of a patterned semiconductor wafer. FIG. 5A illustrates a top view of the wafer 500. As shown, the wafer 500 may be divided up into individual dies 502a, 502b, and 502c. A plurality of predetermined measurement locations 504a, 504b, 504c may also be provided. These measurement locations are typically situated in areas on the surface of wafer 500 which are between adjacent dies. The reason is these areas tend to have areas that are designed to be used as measurement locations. This can be seen from an examination of FIG. 5B, which illustrates an example of a cross-section of one of the dies of FIG. 5A. As illustrated, in this example, the cross-section has three layers, identified from top to bottom respectively with identifying numerals 506a, 506b, and 506c. A combination of features provided in layers 506b and 506c form field-effect transistors 514a, 514b, and 514c. Layer 506c in this example provides doped regions 506a, 506b, 506c within a silicon substrate, where the doped regions 506a, 506b, 506c serve as the source/drain regions, respectively, of transistors 514a, 514b, and 514c. Layer 506b in this example comprises regions 510a, 510b, 510c which serve at the gates, respectively, of transistors 514a, 514b, and 514c. The topmost layer 506a provides metal contact regions 512a, 512b, 512c which may be selectively connected to individual ones of gate regions 510a, 510b, 510c during the processing of the die.

This cross-section is built up layer by layer in the following order: 506c, 506b, and 506a. During or after the process of adding each of the layers, 506a, 506b, 506c, it may be desirable to measure the thickness of the layer at one or more points. However, it will be seen that each of the layers includes features which make it difficult to precisely model the reflectance spectra at those locations. For example, layer 506c has source/drain regions 508a, 508b, and 508c; layer 506b has gate regions 510a, 510b, 510c; and layer 506a has contact regions 512a, 512b, and 512c. These features compound the problem of modeling the reflectance spectra at these areas within the die. To simplify the modeling process, then, predetermined measurement locations are determined in areas where there are typically less features present, thereby simplifying the modeling process. In FIG. 5A, examples of these locations are the locations identified with numerals 504a, 504b, 504c. Most often, open areas approximately 100 µm×100 µm are included in the wafer pattern design to serve as locations for film property measurements.

Figure 6A:
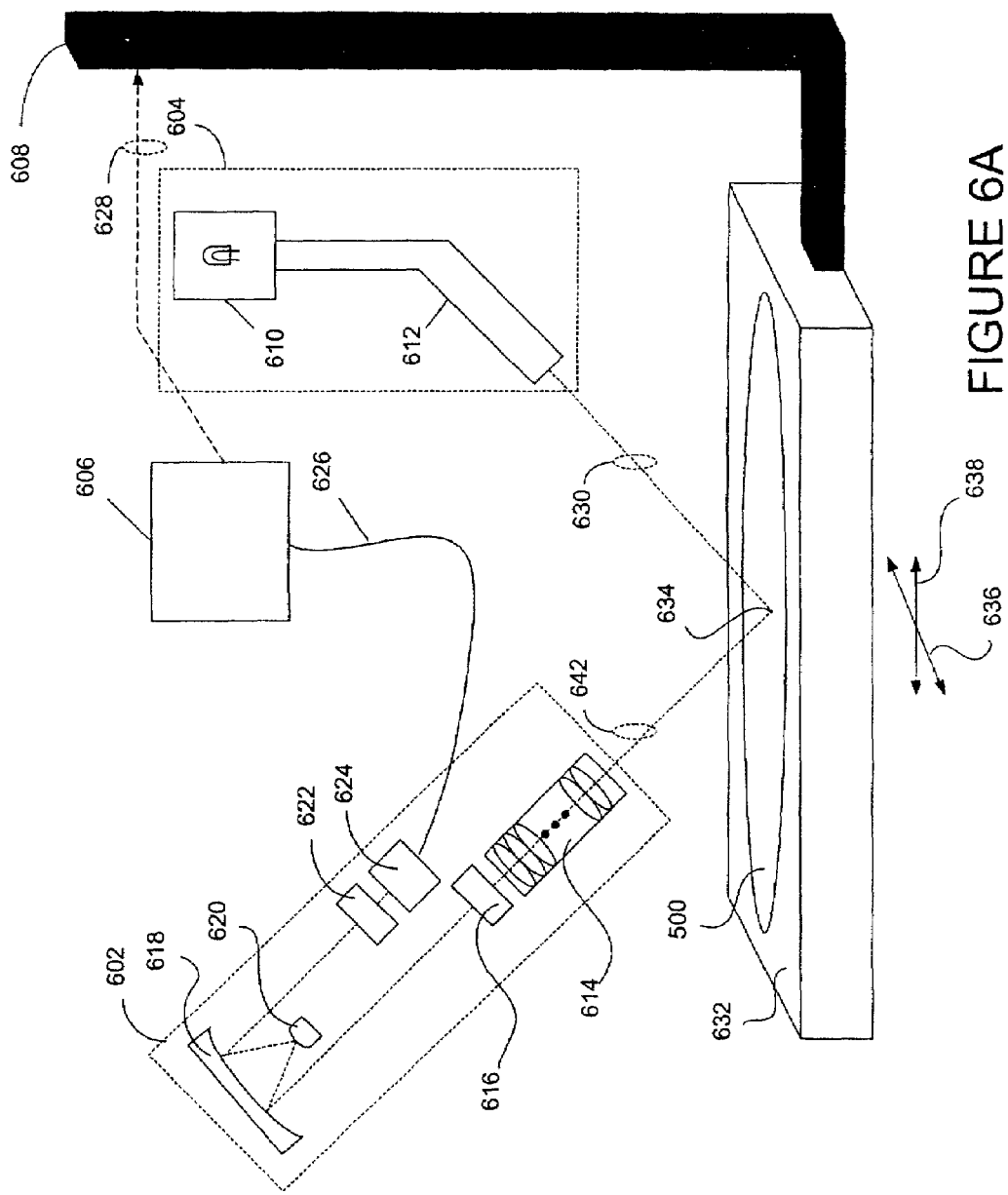
FIG. 6A illustrates a commercial embodiment of a system according to the invention.

FIG. 6A illustrates an overall view of the commercial embodiment 600 of the system. A wafer 500 is supported on platform 632. A light source 604 directs light 630 to a plurality of locations 634 on the surface of the wafer 500, which, in the current commercial embodiment, is in the form of a line which spans the entire diameter of the wafer 500. It should be appreciated, however, that embodiments are possible where the plurality of locations 634 form a one dimensional pattern other than a line, form a non-linear line such as an irregular or curved line or pattern, or form a line which spans less than the full diameter of wafer 500.

Figure 7:
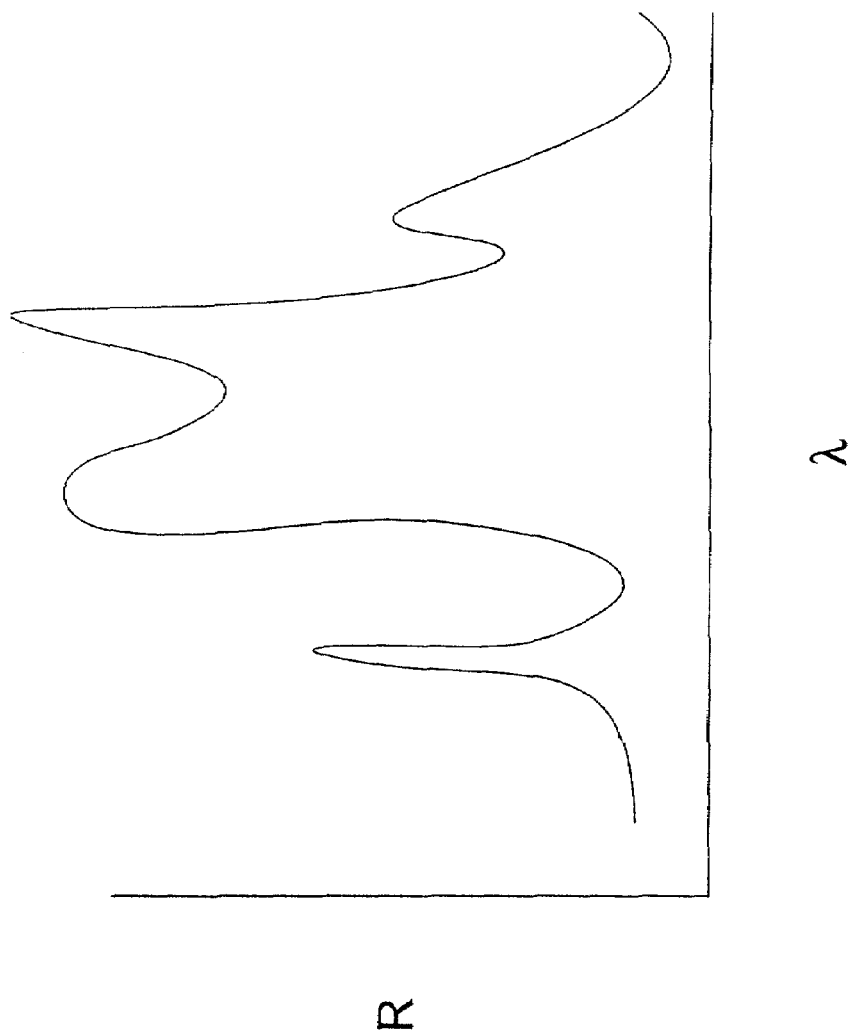
FIG. 7 illustrates an example of a reflectance spectrum for a location on the surface of a semiconductor wafer.

A one dimensional imaging spectrometer 602 receives the reflected light from the one or more locations 634, and determines therefrom the reflectance spectra representative of one or more of the locations 634. The reflectance spectrum for a location is the spectrum of the intensity of the reflected light from the location as a function of wavelength, or some other wavelength-related parameter such as $1/\lambda$, $n/\lambda$ or $nd/\lambda$, where n is the index of refraction for the material making up the layer, $\lambda$ is wavelength, and d is the thickness of the layer. An example of the reflectance spectrum for a location on the surface of wafer 500 may be as illustrated in FIG. 7.

Once determined, the reflectance spectra for the plurality of locations 634 is provided to processor 606 over one or more signal lines 626, which may be implemented as a cable or other wireline connection, or as a wireless connection or interface, or an optical interface or communication link. This data may be provided to the processor concurrently with the capture of data from other locations on the surface of wafer 500. Alternatively, this transfer may be deferred until data for all or a substantial portion of the surface of wafer 500 has been captured.

A translation mechanism 608 is configured to relatively translate wafer 500 relative to spectrometer 602 and light source 604 (or just spectrometer 602) so that the incident light 630 can be scanned across the entirety of the surface of wafer 500. The translation mechanism 608 may be under the control of processor 606 or some other control means. In the current commercial embodiment, control of translation mechanism 608 is provided by processor 606, as indicated by the phantom line 628. Also, in the current commercial embodiment, where the incident light 630 impinges on the surface of wafer 500 in the form of a line which spans the full diameter of the wafer, the wafer 500 need only be moved in the X direction, identified with numeral 636, but it should be appreciated that embodiments are possible in which other directions of scanning, or combinations of directions, are possible. For example, in the case where the incident light impinges on the surface of wafer 500 in the form of a line which spans half of the fall diameter of the wafer, the wafer 500 may be scanned in its entirety by scanning one half of the wafer in the X direction, then translating the wafer in the Y direction (identified with numeral 638) so that the remaining unscanned portion of the wafer 500 resides under the incident light, and then scanning the second half of the wafer 500 by translating the wafer 500 in the X direction.

Figure 8:
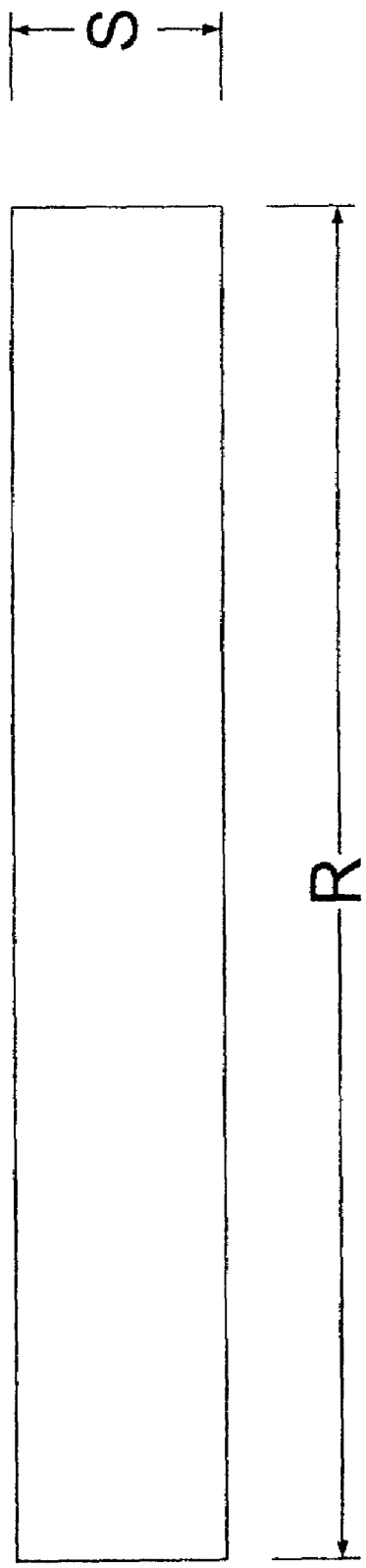
FIG. 8 illustrates a cross section of the fiber bundle of the system of FIG. 6A.

In the current commercial embodiment, where the plurality of locations 634 is in the form of a line which spans the full diameter of wafer 500, the light source 604 and spectrometer 602 are in a fixed relationship relative to one another, and the translation mechanism 608 is configured to achieve relative translation between the spectrometer 602 and the wafer 500 by successively moving the platform 632 supporting the wafer 500 relative to the light source 604 and spectrometer 602 in the X direction, identified with numeral 636. However, it should be appreciated that embodiments are possible in which light source 604 and spectrometer 602 are moveable relative to the wafer 500 by moving the light source 604 and spectrometer 602 relative to the platform 632. An embodiment is also possible where the light from light source 604 impinges on the entirety of the surface of the wafer 500, and it is only necessary to relatively translate the wafer 500 relative to the spectrometer 602. In the current commercial embodiment, the light source 604 comprises a white light source 610, or at least a light source having wavelength components over a desired wavelength range. In this commercial embodiment, light source 604 also includes a light shaper 612, which may be in the form of a fiber cable bundle where the individual fibers at the outer face 640 of the cable in aggregate form a rectangular shape as shown in FIG. 8. The rectangular shape of outer face 640 serves to project light from source 610 onto the surface of wafer 500 in the form of a line in the Y direction which spans the full diameter of the wafer, which in the case of this example is 100 mm. With reference to FIG. 8, the number of fibers currently employed in the long dimension, identified in the figure as R, is currently about 10,000 fibers, and S, the number of fibers in the short dimension, is currently about 10, but it should be appreciated that other dimensions and shapes are possible depending on the application. It should also be appreciated that embodiments are possible in which light shapers other than fiber cables are employed, or where light shapers are avoided.

The spectrometer 602 in the current commercial embodiment includes a lens assembly 614 situated along the optical path traced by the reflected light 642 from the surface of wafer 500. This lens assembly 614 functions to reduce the size of the reflected light from about a 100 mm line to about a 26 mm line.

A slit 616, concave mirror 618, and convex mirror 620 are also included within spectrometer 602, and are also placed along the optical path traced by the reflected light 642. In the current commercial embodiment, these optical elements are placed after lens assembly 614 in the order shown in FIG. 6A. The slit 616 functions to aperture the light emerging from lens assembly 614 so that it is in the form of a line, and mirrors 618 and 620 function to direct the light so that it impinges upon transmission diffraction grating 622 which next appears along the optical path. As previously discussed, the entire lens/slit/mirror assembly is of sufficient quality that the MTF for an alternating black and white line pattern having a density of 40 line pairs/mm is not less than 70%.

It should be appreciated that lens assembly 614, slit 616, and mirrors 618 and 620 are not essential to the invention, and that embodiments are possible where these components are avoided entirely, or where other optical components are included to perform the same or similar functions.

In one embodiment, the spectrometer 602 is configured to concurrently or simultaneously capture a reflectance spectrum for each of a plurality of spatial locations on the surface of a sample. The spectrometer includes a wavelength-dispersive element, such as a prism or diffraction grating, for receiving in parallel light representative of the plurality of spatial locations, and concurrently or simultaneously separating the light for each such location into its constituent wavelength components. The spectrometer further includes an imager for receiving the constituent wavelength components for one or more of the locations, and determining therefrom the reflectance spectrum for each such location. For purposes of this disclosure, the terms "simultaneously", "concurrently", and "parallel" do not require precise temporal exactness, but allow some leeway in precise temporal exactness to account for relative delays that are acceptable in the trade, such as relative delays that do not interfere with real time operation of the device (in one implementation, delays less than 1 mSec. are permissible).

Figure 6B:
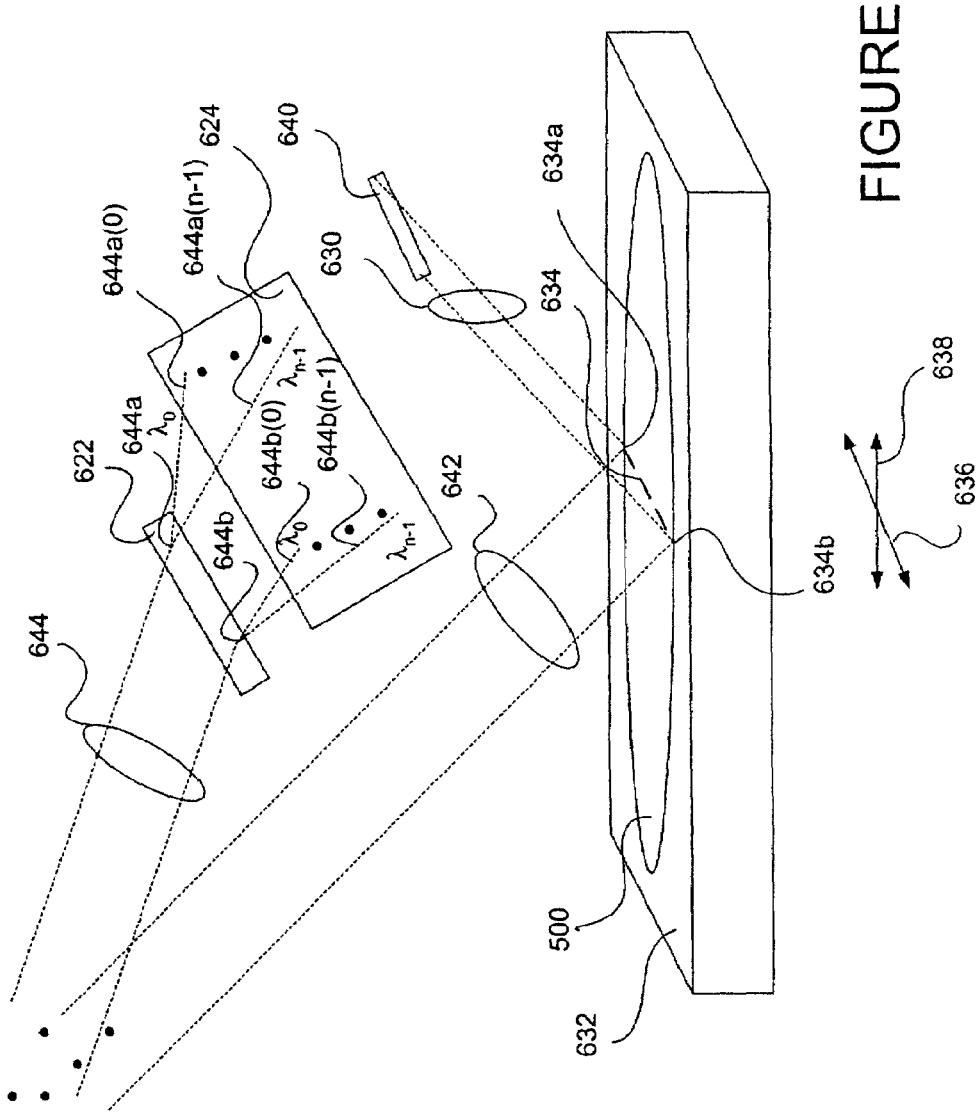
FIG. 6B illustrates aspects of the optical path of the system of FIG. 6A.

In the current commercial embodiment, the light which impinges on diffraction grating 622 is located close to the CCD imager and is thus close to being focused back into the form of a line. The situation is as depicted in FIG. 6B in which, relative to FIG. 6A, like elements are identified with like reference numerals. As illustrated, incident light 630 from the outer face 640 of light shaper 612 is in the form of a line, and impinges upon wafer 500 in the form of a line 634 which spans the full diameter of the wafer 500 in the Y direction 638. The reflected light 642 is also in the shape of a line, and after various resizing and shaping steps, impinges upon diffraction grating 622. The line 644 is divisible into portions, each of which is representative of corresponding portions of wafer 500 along line 634. For example, portion 644a of the light impinging on diffraction grating 622 is representative of portion 634a of wafer 500, and portion 644b of the impinging light on diffraction grating 500 is representative of portion 634b of wafer 500.

Diffraction grating 622 breaks each of the individual portions of line 644 into their constituent wavelengths. Thus, with reference to FIG. 6B, grating 622 breaks portion 644a into n wavelength components, $\mu_0, \ldots, \mu_{n-1}$, identified respectively with numerals 644a(0), ..., 644a(n−1), and also breaks portions 644b into n wavelength components $\lambda_0, \ldots, \lambda_{n-1}$, identified respectively with numerals 644b(0), ..., 644b(n−1).

The wavelength components from each of the portions of line 644 impinge on imager 624, which measures the intensity of each of these wavelength components. Imager 624 then provides data representative of each of these intensities to processor 606.

In the current commercial embodiment, imager 624 has a resolution of 2048 pixels by 96 pixels, although in the current commercial embodiment, only 32 pixels in the vertical (spectral) dimension are used. In the spatial dimension, the sensor 602 is imaging about 100 mm of the wafer onto the 2048 pixels of the imager 624, which corresponds to approximately 50 µm of the wafer surface being imaged onto each pixel. The width of the slit 616 in the spectral dimension determines the measurement spot size in the direction perpendicular to the line image, and it was chosen so that the spot size is 50 m in this dimension as well, so the resulting measurement spot size is approximately 50 µm×50 µm square over the entire 100 mm line being measured on the wafer. Additional commercial embodiments, such as the Filmetrics STMapper, measure larger wafers with the same sensors by simply mounting multiple sensors side-by-side to measure contiguous 100-mm-wide swathes of the wafers simultaneously. For example, the very common 200 mm diameter wafers are measured by mounting two sensors side-by-side, and the larger 300 mm diameter wafers are measured by mounting three sensors side-by-side.

Through the foregoing combination of features, including the number of pixels in the CCD imager and the aperature slit size, the spectrometer 602 may provide a resolution of 1 mm or better in first or second spatial dimensions, such as the X and Y dimensions 636 and 638. In the current commercial embodiment, a resolution of about 50 µm. is provided in both X and Y dimensions.

Figure 9:
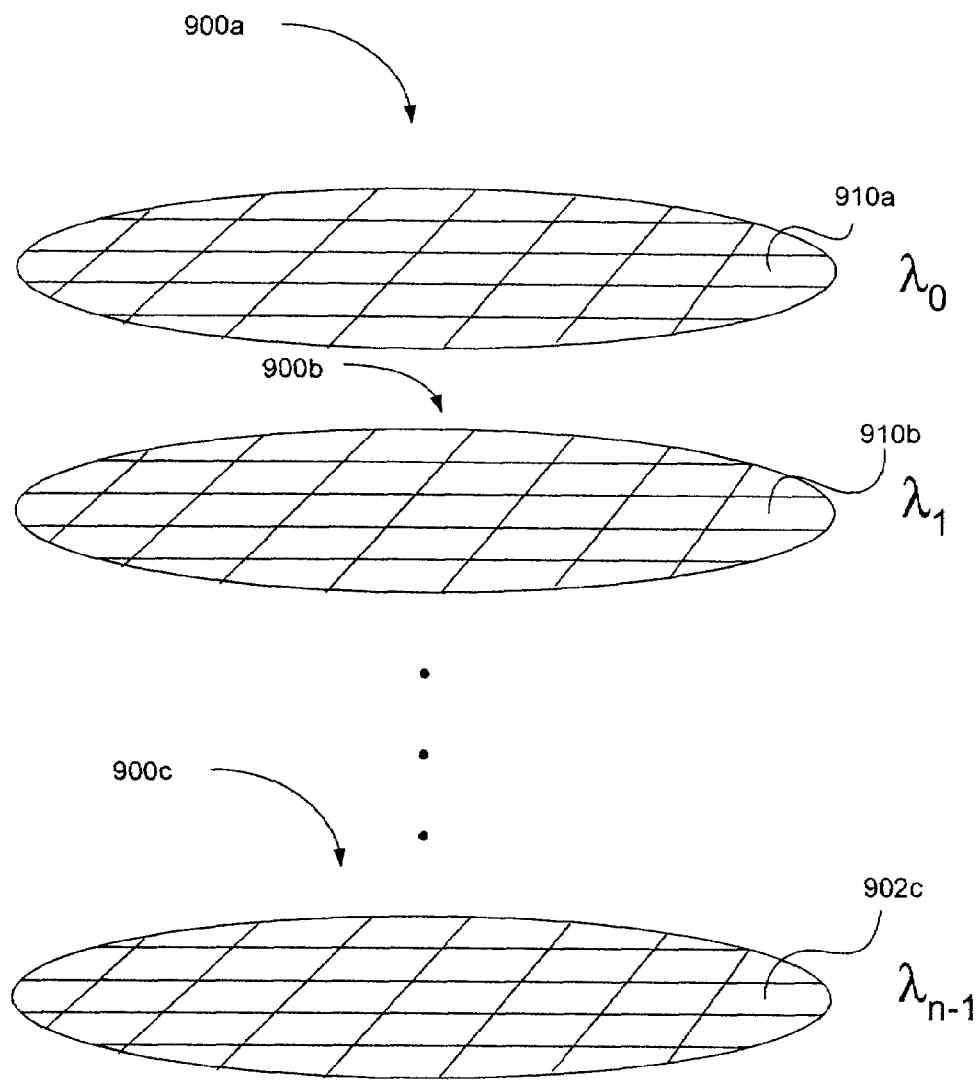
FIG. 9 depicts the data which is captured for an individual layer in the system of FIG. 6A.

Once the scanning of a layer has been completed, the processor 606 will have access to the reflectance spectra for all or a substantial portion of the entire surface of wafer 500. This data can be depicted as shown in FIG. 9. Numeral 900a identifies the reflectance data for the first wavelength component, $\lambda_0$, numeral 900b identifies the reflectance data for the second wavelength component, $\lambda_1$, and numeral 900c identifies the reflectance data for the (n−1)th wavelength component, $\lambda_{n-1}$. In the current commercial embodiment, there are 32 wavelength components provided for each pixel location. The collection of these wavelength components constitutes the reflectance spectrum for the pixel location. Thus, with reference to FIG. 9, the wavelength components identified with numerals 902a, 902b, 902c, collectively constitute the reflectance spectrum for a pixel on the surface of the wafer. Currently, about 1 Gbyte of data is generated for each layer, so the processor must include a storage device which is capable of storing this quantity of data. This data may have spatial resolution of 1 mm or better. In the current commercial embodiment, the data has spatial resolution of about 50 µm. For purposes of this disclosure, the terms "about" and "approximately" are intended to allow for tolerances that are acceptable in the trade. In one implementation, tolerances of ±25% are possible.

Once the data for a layer has been captured, processor 606 is configured to analyze the data and determine therefrom the thickness or other property of the layer at one or more desired measurement locations. In the current commercial embodiment, the coordinates of these measurement locations are known, and accessible to the processor 606. These coordinates are typically defined in relation to one or more reference points on the wafer, such as the center of the wafer and an orientation notch at the edge of the wafer. The processor 606 may orient the spectral data for the wafer by locating the center of the wafer and the orientation notch by analyzing the two dimensional reflectance or transmission map. For example, the processor 606 may use image processing to locate the edge of the wafer and then locate the center as the location which is equidistant from the edge. It may then find the notch, again using image processing. Once this orientation has occurred, the processor 606 may then apply the coordinates of the measurement locations to the acquired data.

The processor 606 also has access to information which describes the structure of the wafer at the desired measurement locations sufficiently to allow the reflectance spectra at the desired locations, or the immediately surrounding areas, to be accurately modeled. Such information might include the composition of the layer in question and that of any layers below the layer in question, a description of any features, such as metal leads and the like, present in the layer in question and in any layers below the layer in question, and the thicknesses of any layers below the layer in question. For each of the desired measurement locations, the processor 606 is configured to use this information to model the reflectance spectrum of that location, or surrounding areas, assuming a thickness for the layer in question.

As one of skill in the art would appreciate, once the structure and properties of a film or film stack are known, the reflectance (or transmission) spectra for a location on a film or film stack may be easily modeled through application of the Fresnel equations. Moreover, the effect on the reflectance (or transmission) spectrum of varying one or more of the film properties may also easily be modeled, again through application of the Fresnel equations. Therefore, it is unnecessary to describe the modeling process in great detail, and the reader is referred to various web pages, e.g., http://www.treasure-troves.com/physics/FresnelEquations.html, for additional information on the Fresnel equations, or to various texts, such as "Spectroscopic Ellipsometry and Reflectometry: A User's Guide," by Harland G. Tompkins and William A. McGahan, John Wiley & Sons, Inc., New York, 1999, for additional information on modeling reflectance or transmission spectra through application of the Fresnel equations. The foregoing web page, as well as the foregoing Tompkins and McGahan text, are hereby fully incorporated by reference herein as through set forth in full.

The processor 606 is further configured to compare the modeled spectrum for a desired measurement location, or location within a surrounding area, with the actual reflectance spectrum for this or surrounding locations, and if the modeled spectrum is within a defined tolerance of the actual spectrum, determine that the assumed layer thickness is the actual layer thickness. If the comparison is not within the defined tolerance for the measurement location in question, the processor 606 is configured to either (a) vary the assumed layer thickness and remodel the reflectance spectrum using the new assumed layer thickness, or (b) vary the location from which the actual reflectance spectrum is taken. Processor 606 may then re-perform the comparison until the modeled and actual data are within the prescribed tolerance. Alternatively, the processor 606 may perform this comparison for each of the pixels in a predetermined area surrounding a nominal desired measurement location, e.g., a 10×10 pixel area, and determine which of the locations provides the closest fit between actual and modeled data. The assumed property value which provides the closest fit may be taken as the actual property value for the predetermined location. In another alternative, for each of the pixels within the surrounding area, the processor 606 may vary the assumed property until the best possible fit is obtained between the modeled and actual data. It may then compare the fit for each of these pixels, and select the pixel with the closest possible fit. Again, the assumed property value which provides the closest possible fit may be taken as the actual value for the desired measurement location. In a variant of this alternative, the top 5 (or other predetermined number) of the pixels which provide the best fit are selected, and the assumed property values for these pixels are averaged to determine the value taken as the actual property value for the predetermined measurement location. The processor 606 is configured to repeat this process for each of the desired measurement locations on a layer. This process may be performed in relation to other properties besides layer thickness, including optical properties or doping properties, such as index of refraction, extinction coefficient, etc.

Figure 10:
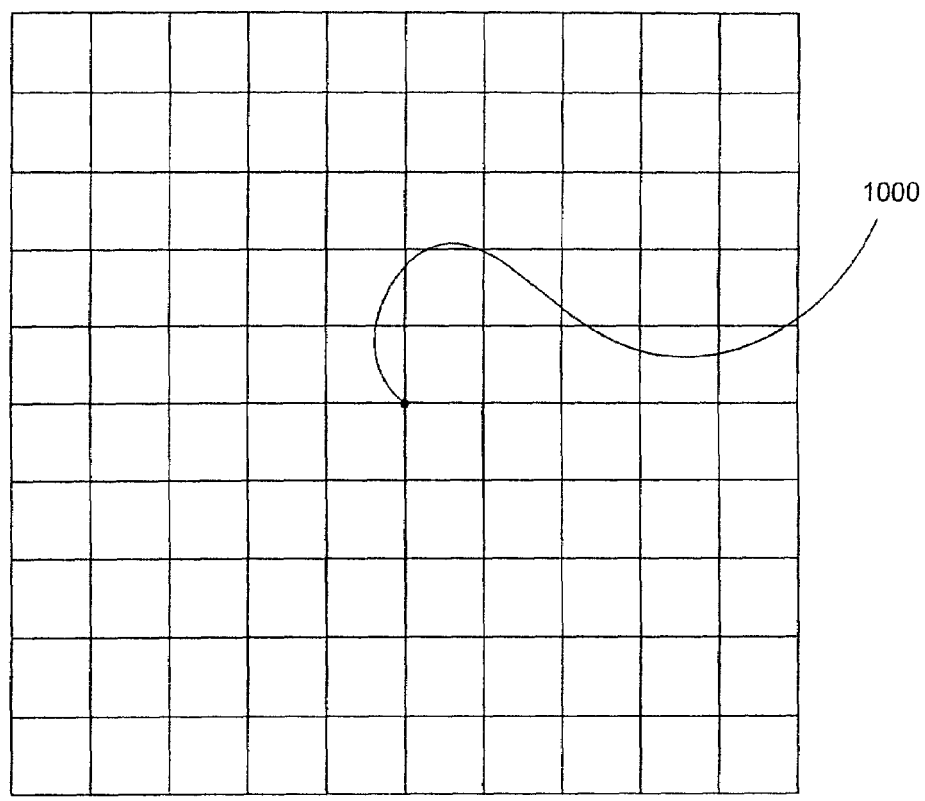
FIG. 10 illustrates the area surrounding a desired measurement location in which matching is performed in the system of FIG. 6A.

In the current commercial embodiment, the processor 606 performs the comparison over a 10×10 pixel area centered around the nominal position of the desired measurement location, but it should be appreciated that other areas are possible. More than one pixel is generally required to be analyzed because there is some uncertainty in the exact location of the desired measurement spot relative to the acquired wafer image, due to image imperfections caused by wafer vibration or other non-idealities. The situation is illustrated in FIG. 10, which illustrates the 10×10 pixel area surrounding the nominal desired measurement location 1000. The processor 606 is configured to compare the modeled spectrum with the measurement spectrum for each of these pixels, and to compute a running sum for each of the pixels of the absolute value of the difference for each wavelength component of the spectra. Mathematically, this process can be represented as follows for a single pixel:

$$RSum = \sum_{i} ABS(\Delta_i) \quad (1)$$

where the index i ranges over all possible wavelength components for a given pixel (currently 32), $\Delta_i$ is the difference between the modeled and actual intensities of the ith wavelength component for the pixel being analyzed, and ABS is the absolute value function. The modeled data for the pixel within this 10×10 area that provides the closest fit may be used to determine the one or more film properties for the desired measurement location. Alternatively, the modeled data for the first pixel in this area that is within a predetermined threshold of the actual data for the location may be used to determine the one or more film properties for the desired measurement location. However, it should be appreciated that other methods of performing the comparison are possible and within the scope of the invention, such as the methods described above in relation to processor 606, or methods in which less or more than a 10×10 area is involved, in which the comparison is performed over an area that is not necessarily centered on a desired measurement location, and in which functions other than the ABS function are employed. For example, in one alternative, the following statistic may be employed:

$$RSum = \sqrt{\sum_{i} \Delta_i^2} \quad (2)$$

Figure 11:
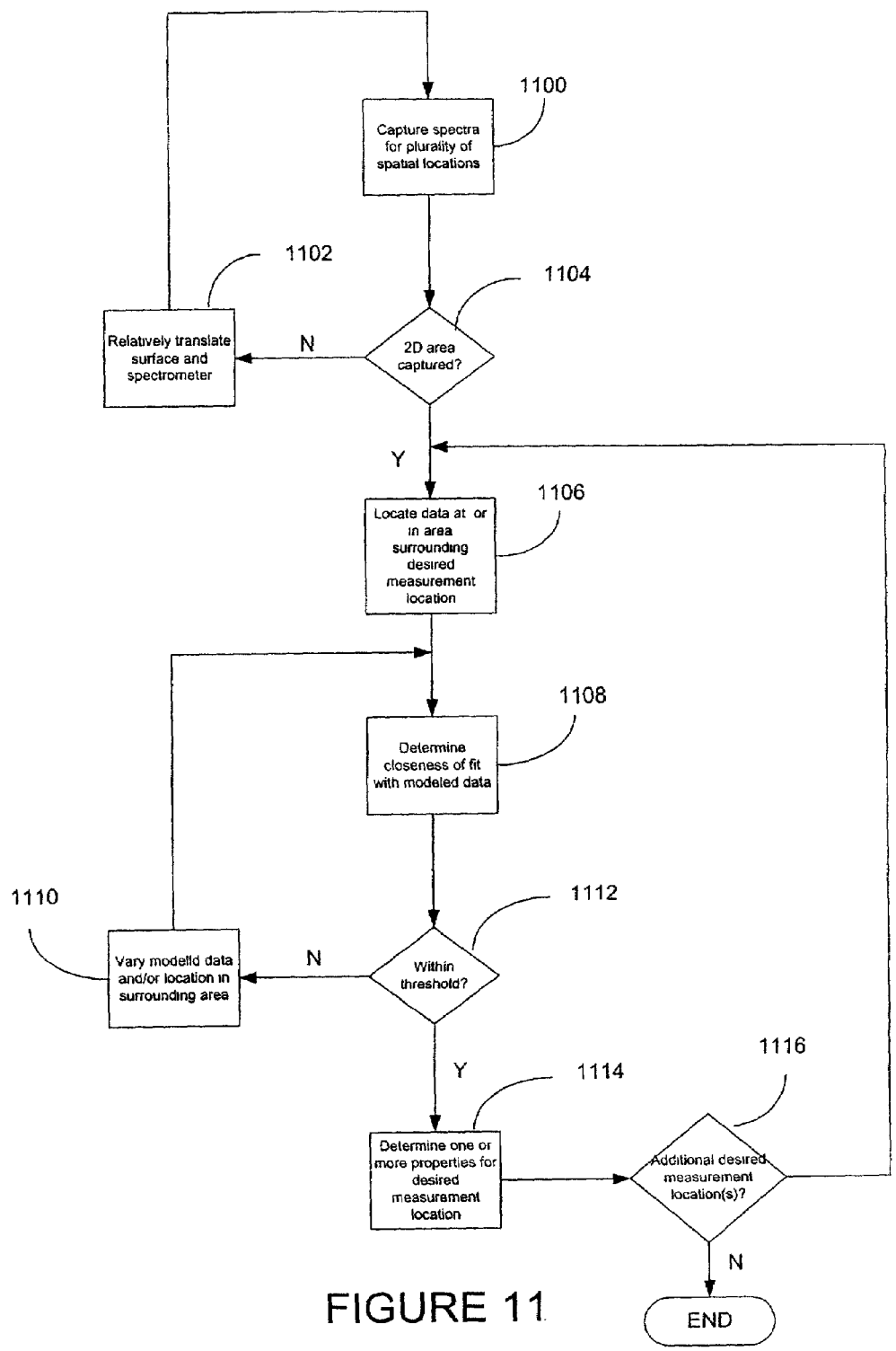
FIG. 11 is a flowchart of an embodiment of a method of operation in the system of FIG. 6A.

FIG. 11 is a flowchart of the method of operation followed by the current commercial embodiment for one or more layers in the sample being evaluated. The sample may be a semiconductor wafer or some other sample. In step 1100, the reflectance spectra for a plurality of spatial locations on a sample are captured. The spatial locations may be in the form of a line, either linear or non-linear, or some other one dimensional shape or pattern, such as a curved shape, although in the current commercial embodiment, the locations are in the form of a line.

In step 1004, an evaluation is made whether all or a substantial portion of a two dimensional area on the sample has been scanned. If not, step 1102 is performed. In step 1102, a relative translation is performed between the sample and the spectrometer used to perform the capture process. Again, this step can occur by moving the sample relative to the spectrometer or vice-versa. It may also include moving the sample relative to the light source and spectrometer, or vice-versa. Step 1100 is then re-performed, and this process repeated until all or a substantial portion of the two dimensional area has been scanned.

When all or a substantial portion of the two dimensional area has been scanned, step 1106 is performed. In step 1106, the coordinates of a desired measurement location are used to locate the reflectance data for that location or a location within a surrounding area. Step 1108 is then performed. In step 1108, the reflectance data for the location or a location within the surrounding area is compared with modeled reflectance data for that location or a location within the surrounding area to determine if the modeled data and actual data are within a prescribed tolerance. This modeled data is determined assuming a particular property for that layer at or near the desired measurement location.

The closeness of the fit is evaluated in step 1112. If the fit is outside a prescribed tolerance, step 1110 is performed. In step 1110, the reflectance data for the location is re-modeled assuming a different assumed layer property and/or the location from which the actual data is taken is varied. Steps 1108 and 1112 are then re-performed. This process then continues until the modeled data is within the prescribed tolerance of the actual data. Step 1114 is then performed. In step 1114, the assumed layer property for the modeled data which satisfied the tolerance criteria in step 1112 is taken to be the actual layer property at the desired location.

Alternatively, in lieu of steps 1108, 1110, and 1112, the actual data may be compared to the modeled data for each of the locations in a predetermined area surrounding and including a nominal measurement location, e.g., 10×10 pixel area. For each such pixel, the assumed property value may be varied until the best possible fit is obtained. The pixel within the group which provides the closest fit is selected, and the assumed layer property for that location is taken to be the layer property for the desired measurement location. In a further variant, this value is taken to be the layer property at the desired location only if the fit is within a predetermined tolerance. Other variants and alternatives are possible, as described above in relation to processor 606 and elsewhere.

Step 1116 is then performed. In step 1116, it is determined whether there are additional desired measurement locations for the layer in question. If so, a jump is made back to step 1106, and the process then repeats from that point on for the next location. If not, the process ends.

The foregoing commercial embodiment has been described and illustrated in terms of receiving reflected light from a film, and determining reflectance spectra for various spatial locations on the film, but it should be appreciated that embodiments are possible where light is transmitted through a film, the transmission spectra for one or more spatial locations on the film are determined and aggregated to form transmission spectra for a two dimensional area on the film, and one or more properties of the film determined from the transmission spectra for the two dimensional area in like manner to the foregoing commercial embodiment. Therefore, these embodiments employing transmission spectra are also within the scope of the invention.

Additional advantages and modifications will readily occur to those of skilled in the art. The invention in the broader aspects is not, therefore, limited to the specific details, representative methods, and illustrative examples shown and described. Accordingly, departures may be made from such details without departing form the spirit or scope of applicant's general inventive concept, and the invention is not to be restricted except in light of the appended claims and their equivalents.

The invention claimed is:

1. A system that acquires and analyzes spectral images of a wafer, the system comprising:
   a plurality of stations;
   a transfer mechanism operable to transfer the wafer between each of the plurality of stations;
   an illumination source that illuminates the wafer as the wafer is transferring between the plurality of stations;
   a spectral imager configured to detect light of the illumination source that is reflected from the wafer as the transfer mechanism is transferring the wafer between the plurality of stations, the spectral imager configured to produce a plurality of one-dimensional spectral frames using information of the light reflected from the wafer as the wafer is transferring between the plurality of stations; and
   circuitry for analyzing said plurality of one-dimensional spectral frames and aggregating at least one of the one-dimensional spectral frames to form two-dimensional spectral images.

2. The system of claim 1, wherein the wafer includes a substrate and at least one layer of at least one thin film on the substrate, wherein the at least one thin film includes a plurality of properties, wherein the plurality of properties comprise a thickness value of the at least one layer at one or more sites on the wafer.

3. A method for imaging a wafer having one or more film layers, comprising:
   illuminating the wafer with light;
   positioning the wafer so that a portion of the wafer is illuminated;
   detecting light reflected from the portion of the wafer using a spectral imager configured to produce a sequence of one-dimensional spectral frames while the spectral imager and the wafer undergo relative motion provided by a transfer mechanism moving the wafer between a plurality of stations;
   aggregating said sequence of one-dimensional spectral frames to form a two-dimensional spectral image, and analyzing said two-dimensional image to determine a property of the film layers.

4. The method of claim 3, wherein the property is a thickness value of one of the one or more film layers at one or more sites on the wafer.

5. A CMP system that images a wafer, comprising:
   a plurality of stations for performing one or more aspects of a CMP process;
   a wafer transfer mechanism disposed within the system to transfer the wafer between said stations;
   a light source for illuminating the wafer while the wafer transfer mechanism is transferring the wafer between the stations;
   a spectral imager disposed to detect light from the light source that is reflected from the wafer and configured to produce a plurality of one-dimensional spectral frames while said spectral imager and the wafer undergo relative motion provided by said wafer transfer mechanism; and
   circuitry for processing said plurality of one-dimensional spectral frames, wherein the circuitry aggregates sequential one-dimensional spectral frames to form a two-dimensional spectral image, and analyzes said two-dimensional spectral image to determine one or more properties of one or more film layers of the wafer.

6. The system of claim 5, wherein the one or more properties include a thickness value of one of the one or more film layers at one or more sites on the wafer.

7. A method for imaging a wafer having one or more film layers, comprising:
   illuminating the wafer with light;
   positioning the wafer so that a portion of the wafer is illuminated;
   detecting light reflected from the portion of the wafer using a spectral imager configured to produce a sequence of spatially contiguous one-dimensional spectral frames while said spectral imager and the wafer undergo relative motion provided by a transfer mechanism used to move wafers between stations; and
   aggregating said frames to form a two-dimensional spectral image.

8. The method of claim 7, further comprising analyzing the two-dimensional spectral image, wherein analyzing determines a film layer thickness value of one of the one or more film layers at one or more sites on the wafer.

9. A semiconductor wafer processing system that acquires and analyzes spectral images of a wafer prior to, during, and/or following a process, the system comprising:
   a plurality of stations;
   a wafer transfer mechanism disposed within the system to transfer the wafer between the stations;
   a light source for illuminating the wafer while the wafer is transferred between said stations;

a spectral imager disposed to detect light from the light source that is reflected from the wafer, the spectral imager configured to produce a plurality of one-dimensional spectral frames while said spectral imager and the wafer undergo relative motion provided by said wafer transfer mechanism; and a processor for analyzing said plurality of one-dimensional spectral frames, wherein the processor aggregates sequential one-dimensional spectral frames to form two-dimensional spectral images.

10. The system of claim 9, wherein the process includes one or more of a CVD process, a CMP process, or a stand-alone metrology process.

11. The system of claim 9, wherein the stations include one or more of a load station, an unload station, or a process station.

12. The system of claim 9, wherein the lights source is one of pulsed or continuous while said spectral imager detects light.

13. A semiconductor wafer processing system that provides and analyzes spectral images of a wafer having one or more film layers prior to, during, and/or following a process, the system comprising:

a wafer transfer mechanism disposed within the system to transfer the wafer between a load station and a wafer chuck;

a light source for illuminating the wafer while the wafer is transferred between said load station and said wafer chuck;

a spectral imager disposed to detect light reflected from the wafer and configured to produce a one-dimensional spectral frame while said spectral imager and the wafer undergo relative motion of transferring the wafer; and a processor that analyzes said one-dimensional frame.

14. A semiconductor wafer imaging system that acquires and analyzes spectral images of a wafer having one or more film layers, the system comprising:

a first processing system that performs a first manufacturing process on the wafer;

a second processing system that performs a second manufacturing process on the wafer, where said second manufacturing process follows said first manufacturing process;

a wafer transfer mechanism disposed to transfer the wafer between said first processing system and said second processing system;

a light source for illuminating the wafer while the wafer is transferred between said first processing system and said second processing system;

a spectral imager disposed to detect light from the light source that is reflected from the wafer during the transfer, and configured to produce one-dimensional spectral frames; and circuitry for aggregating said one-dimensional spectral frames to form a two-dimensional spectral image and analyzing said two-dimensional spectral image to determine a film layer property of the one or more film layers.

15. The system of claim 14, wherein the one or more film layer properties include a thickness value of one of the one or more film layers at one or more sites on the wafer.

16. A method of obtaining and analyzing a spectral image of a wafer having one or more film layers, the method comprising:

securing the wafer from a first processing system using a transfer mechanism;

illuminating the wafer with light from a light source;

positioning the wafer using said transfer mechanism so that a portion of the wafer is illuminated by light from said light source;

detecting light reflected from said portion of the wafer using a spectral imager configured to produce a sequence of contiguous one-dimensional spectral frames while said transfer mechanism moves the wafer;

aggregating said sequence of contiguous one-dimensional spectral frames to form a two-dimensional spectral image;

analyzing said two-dimensional image to determine one or more film layer properties of the one or more film layers; and transferring the wafer to a second processing system.

17. The method of claim 16, wherein the one or more film layer properties include a thickness value of one of the one or more film layers at one or more sites on the wafer.

* * * * *